United States Patent
Laroia

(10) Patent No.: US 12,156,706 B2
(45) Date of Patent: Dec. 3, 2024

(54) AUTOMATED DEVICE FOR PERFORMING MEDICAL PROCEDURES

(71) Applicant: University of Iowa Research Foundation, Iowa City, IA (US)

(72) Inventor: Sandeep Laroia, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 273 days.

(21) Appl. No.: 17/749,988

(22) Filed: May 20, 2022

(65) Prior Publication Data

US 2022/0370151 A1  Nov. 24, 2022

Related U.S. Application Data

(60) Provisional application No. 63/191,385, filed on May 21, 2021.

(51) Int. Cl.
| | | |
|---|---|---|
| *A61B 34/20* | (2016.01) | |
| *A61B 17/3211* | (2006.01) | |
| *A61B 17/34* | (2006.01) | |
| *A61B 34/32* | (2016.01) | |

(52) U.S. Cl.
CPC .......... *A61B 34/20* (2016.02); *A61B 17/3211* (2013.01); *A61B 17/3403* (2013.01);
(Continued)

(58) Field of Classification Search
CPC . A61B 34/20; A61B 17/3211; A61B 17/3403; A61B 17/3421; A61B 34/32;
(Continued)

(56) References Cited

U.S. PATENT DOCUMENTS

2004/0034339 A1*  2/2004  Stoller ................. A61B 1/3132
                                                        606/1
2008/0033410 A1*  2/2008  Rastegar ............... A61B 34/30
                                                        606/9
(Continued)

FOREIGN PATENT DOCUMENTS

JP           H0698139       * 12/1994

OTHER PUBLICATIONS

M.L. Balter, J.M. Leipheimer, A.I. Chen, A. Shrirao, T.J. Maguire and M.L. Yarmush. Automated end-to-end blood testing at the point-of-care: Integration of robotic phlebotomy with downstream sample processing. Technology vol. 06, No. 02, pp. 59-66 (2018) (Year: 2018).*

(Continued)

*Primary Examiner* — Alexei Bykhovski
(74) *Attorney, Agent, or Firm* — Goodhue, Coleman & Owens, P.C.

(57) ABSTRACT

A system and method for performing an automated medical procedure is provided. The method may include positioning an effector unit over a patient, acquiring medical imagery of the patient, analyzing the medical imagery using at least one processor to determine a location, and positioning a subunit of the effector unit to perform the automated medical procedure at the location. The automated medical procedure may be performed using at least one of a plurality of subunits of the effector unit. The automated medical procedure may be a body fluid aspiration procedure and one of the plurality of subunits of the effector unit may include a fluid aspirating cannula. Multiple subunits may be sequentially used to perform the procedure.

19 Claims, 19 Drawing Sheets

(52) U.S. Cl.
CPC .......... *A61B 17/3421* (2013.01); *A61B 34/32* (2016.02); *A61B 2017/3413* (2013.01); *A61B 2017/3437* (2013.01); *A61B 2034/2055* (2016.02); *A61B 2034/2065* (2016.02)

(58) Field of Classification Search
CPC .... A61B 2017/3413; A61B 2017/3437; A61B 2034/2055; A61B 2034/2065; A61B 34/25; A61B 2017/00225; A61B 2034/302; A61B 2090/063; A61B 2090/378; A61B 2217/005; A61B 17/3415; A61B 34/30
See application file for complete search history.

(56) References Cited

U.S. PATENT DOCUMENTS

2012/0190981 A1* 7/2012 Harris ................... A61B 5/14
604/95.01

2014/0266743 A1* 9/2014 Stacey .................. A61B 90/98
340/4.31

OTHER PUBLICATIONS

Chen, A., Balter, M., Maguire, T. & Yarmush, M. Real-time needle steering in response to rolling vein deformation by a 9-DOF image-guided venipuncture robot. In IEEE/RSJ International Conference on Intelligent Robots and Systems, pp. 2633-2638 (2015) (Year: 2015).*

M.L. Balter, J.M. Leipheimer, A.I. Chen, A. Shrirao, T.J. Maguire and M.L. Yarmush. Automated end-to-end blood testing at the point-of-care: Integration of robotic phlebotomy with downstream sample processing. Technology vol. 06, No. 02, pp. 59-66 (2018) https://doi.org/10.1142/S2339547818500048.

Zivanovic, Aleksandar and Davies, Brian L. A Robotic System for Blood Sampling. Technology in Biomedicine, vol. 4, No. 1, 2000, pp. 8-14.

* cited by examiner

FIG. 17

AUTOMATED DEVICE FOR PERFORMING MEDICAL PROCEDURES

RELATED APPLICATIONS

This application claims priority to U.S. Provisional Patent Application No. 63/191,385, filed May 21, 2021, hereby incorporated by reference in its entirety.

FIELD OF THE INVENTION

The present invention relates to automation of medical procedures. More particularly, but not exclusively, the present invention relates to an automated body fluid aspiration device.

BACKGROUND

Although the background provided herein focuses primarily on abnormal accumulation of fluid and aspiration, it is to be understood that the present invention is not to be limited to this specific context as embodiments may be used in a variety of different situations.

In the context of abnormal accumulation of fluid, one skilled in the art would recognize that abnormal accumulation of fluid in various body cavities is a common occurrence in various disease states, e.g. ascites (accumulation of fluid in the abdominal cavity) which can happen in liver failure, various cancers, and numerous other diseases. Similarly, fluid can accumulate in the chest cavity (pleural effusions) because of cancer or trauma and can be life threatening. The current practice is to aspirate these fluid accumulations manually.

Yet problems remain with such an approach. First, skilled individuals may not be readily available to perform these procedures or there may be a delay in obtaining access to a skilled individual to perform the necessary procedures. This may be particularly true in rural or remote areas or other under-served communities. Where there is lack of experience, the manual process may be more time consuming and may suffer from low accuracy. Where there is delay, the body fluid may continue to accumulate which may increase the threat to the patient's life or otherwise increase risks of adverse effects.

What is needed is a system which provides for automated medical procedures such as, but not limited to, body fluid aspiration which is more accurate and faster than a human performed procedure.

SUMMARY

Therefore, it is a primary object, feature, or advantage to improve over the state of the art.

It is a further object, feature, or advantage to provide a system which can autonomously perform medical procedures such as body fluid aspiration with minimal human supervision.

It is a still further object, feature, or advantage to provide a system which can autonomously perform medical procedures in a manner consistently more accurate than a human performed procedure.

It is another object, feature, or advantage to provide a system which can autonomously perform a medical procedure faster than a human.

It is yet another object, feature, or advantage to provide a system which can perform a medical procedure without requiring the supervisor performing the medical procedure to have a high level of expertise in manually performing the same medical procedure.

Another object, feature, or advantage is to provide a system with a gantry which may be controlled in three dimensions.

Another object, feature, or advantage is to provide a system with a gantry which is light weight.

Another object, feature, or advantage is to provide a system with a gantry which is easy to assemble.

Another object, feature, or advantage is to provide a system with a gantry which has a patient friendly design.

Another object, feature, or advantage is to provide a system with a gantry which is compatible with existing bed systems.

Yet another object, feature, or advantage is to provide a system which may use imaging such as ultrasound imaging.

A further object, feature, or advantage it to provide a system which allows for real-time artificial intelligence (AI) driven image analysis.

A still further object, feature, or advantage is to provide a system which arranges components around a sensing unit.

Another object, feature, or advantage is to provide a system which may be operated remotely.

Yet another object, feature, or advantage is to provide for identification of a target for fluid aspiration using multiple types of sensors such as mechanical (touch), optical and ultrasound mediated sensors.

A further object, feature, or advantage is to provide a systems in which an effector unit may move in an automized fashion after identification of a target.

A still further object, feature, or advantage is to provide for automized and sequential activation of various subunits performing surgical functions and containing appropriate tools such as for needle insertion for administration of local anesthetic, a scalpel blade for skin incision, and insertion of a surgical cannula for fluid aspiration.

Yet another object, feature, or advantage is to provide a system which allows for a reduction in the number of actuators and motors which may assist in reducing size of the system, reducing noise, and reducing sensor signal noise.

Another object, feature, or advantage is to provide for dedicated sequential automatized execution of multiple surgical steps, such as anesthetizing the skin, which is performed by a first subunit, making a skin incision which is performed by a second subunit, and then inserting a surgical tool, e.g. a surgical cannula or needle into the body performed by a third subunit.

Yet another object, feature, or advantage is to provide a system that may be easily adapted to perform any number of different surgical processes.

A further object, feature, or advantage is to provide a system which through changing the tools on this device/robot, multiple diagnostic and therapeutic procedures can be performed in an automatized fashion and these procedures can be controlled locally as well as in a remote fashion.

A still further object, feature or advantage is to provide a device with remote functionality for use in applications where safety of the health care professional is needed. For example in infective pandemic situations like Covid the health care personnel does not get exposed to the infected patient directly.

Another object, feature, or advantage is to provide for automatized injection involving a syringe and needle which may be used to inject toxic radioactive substances or Chemotherapy drugs in a remote fashion without exposing the health care personnel.

Yet another object, feature, or advantage is to provide for a device with a scalpel subunit which may be modified to do other surgical procedures, thereby reducing the work of surgeons.

A further object, feature, or advantage is to provide a surgical cannula or needle used which may be modified to inject treatments in the body. For example, it may be adapted to perform biopsies on tissues or to introduce energy emitting devices like microwave probes, radiofrequency probes, laser probes, etc. in the body for treatment purposes.

A still further object, feature, or advantage is to provide a device for automated medical procedures which may use surgical cannulas to drain abscesses and other body organs, e.g. urinary bladder, obstructed kidneys etc.

Another object, feature, or advantage is to provide a device for automated medical procedures which may perform sequential actions for any number of different diagnostic and therapeutic procedures remotely, e.g. accessing blood vessels to do angiograms, venograms, etc.

One or more of these and/or other objects, features, or advantages will become apparent from the specification and claims that follow. No single embodiment need meet or exhibit each and every one of these objects, features, or advantages as different embodiments may have different objects, features, or advantages whether stated herein or not. Thus, the claimed invention is not to be limited by or to these objects, features, or advantages.

According to one aspect, a system for automated body fluid aspiration is provided. The system may include an effector unit, an ultrasound probe operatively connected to the effector unit, a fluid aspirating cannula subunit operatively connected to the effector unit, and a control unit operatively connected to the effector unit. The control unit may be configured for positioning the effector unit. The control unit may be configured for acquiring imagery from the ultrasound probe and analyzing the imagery to determine a location on a patient to aspirate body fluid. The control unit may be configured for performing automated body fluid aspiration at the location using the fluid aspirating cannula subunit. The system may further include a gantry and wherein the effector unit is operatively connected to the gantry. The gantry may include an arcuate body for arching over the patient. The system may further include a fluid aspiration device fluidly connected to the fluid aspirating cannula subunit. The control unit may be operatively connected to the fluid aspiration device. The performance of the automated body fluid aspiration may include inserting a needle into the patient, inserting the cannula, and monitoring the imagery during aspiration of the body fluid. The control unit may include a display and status of the automated body fluid aspiration may be provided on the display. The control unit may be configured for performing its analysis using a machine learning algorithm. The robotic probe may be configured to rotate. The robotic probe may further include a needle subunit and a scalpel blade subunit.

According to another aspect, a system for automated performance of medical procedures on a patient is provided. The system may include a gantry and an effector unit movably mounted to the gantry such that the effector unit is configured to move along the gantry. The system may further include a sensor probe housed by the effector unit and a plurality of subunits integrated into the effector unit and arranged around the sensor probe wherein each of the subunits comprises a surgical tool. The effector unit may be configured to rotate to re-position the plurality of surgical tools to sequentially target a location. The gantry may include an arcuate body for extending over and across a bed. The plurality of surgical tools may include at least one of an aspiration cannula, a needle, and a scalpel blade. Where the plurality of surgical tools includes an aspiration cannula, and a fluid aspiration device may be fluidly connected to the fluid aspirating cannula. The system may further include a control unit configured to receive imagery acquired using the sensor probe and analyze the imagery in real-time to determine the location. The control unit may be configured to analyze the imagery using artificial intelligence. The sensor probe may be an ultrasound probe.

According to another aspect, a method for performing an automated medical procedure is provided. The method may include positioning an effector unit over a patient, acquiring medical imagery of the patient, analyzing the medical imagery using at least one processor to determine a location, and positioning a subunit of the effector unit to perform the automated medical procedure at the location. The automated medical procedure may be performed using at least one of a plurality of subunits of the effector unit. The automated medical procedure may be a body fluid aspiration procedure and one of the plurality of subunits of the effector unit may include a fluid aspirating cannula.

According to another aspect, a system for automated body fluid aspiration is provided. The system includes an effector unit having a housing, an ultrasound probe operatively connected to the effector unit, a fluid aspirating cannula subunit disposed within the housing of the effector unit, and a control unit operatively connected to the effector unit. The control unit is configured for positioning the effector unit. The control unit is configured for acquiring imagery from the ultrasound probe and analyzing the imagery in determining a target location on a patient to aspirate body fluid. The control unit is further configured for performing automated body fluid aspiration at the location using the fluid aspirating cannula subunit. The system may further include a plurality of sensors operatively connected to the control unit and wherein the control unit is further configured for using data from the plurality of sensors with the imagery in determining the target location on the patient to aspirate the body fluid. The plurality of sensors include at least one touch sensor and at least one optical sensor. The system may further include a gantry and wherein the effector unit is operatively connected to the gantry. The gantry may include an arcuate body for arching over the patient. The system may further include a fluid aspiration device fluidly connected to the fluid aspirating cannula subunit and wherein the control unit is operatively connected to the fluid aspiration device. The performing the automated body fluid aspiration includes inserting a needle into the patient using a syringe subunit of the effector unit, inserting a cannula using the fluid aspiration cannula subunit of the effector unit, and monitoring the imagery during aspiration of the body fluid. The syringe subunit, the fluid aspiration cannula subunit, and the syringe subunit are linearly arranged in the effector unit for sequential operation. The control unit may further include a display and wherein status of the automated body fluid aspiration is provided on the display. The control unit may be configured for analyzing the imagery using a machine learning algorithm. The effector unit may be configured to rotate. The effector unit may further include both a syringe subunit and a scalpel blade subunit.

According to another aspect, a system for automated performance of medical procedures on a patient includes a gantry, an effector unit movably mounted to the gantry such that the effector unit is configured to move along the gantry, a sensor probe operatively connected to the effector unit, and a plurality of subunits integrated into the effector unit wherein each of the subunits comprises a surgical tool. The effector unit is configured to re-position the plurality of subunits to sequentially target a location for the performance of the medical procedure. The gantry may include an arcuate body for extending over and across a bed. The plurality of subunits may include at least one of an aspiration cannula subunit, a syringe subunit, and a scalpel blade subunit. The plurality of surgical tools may include an aspiration cannula and wherein the system further includes a fluid aspiration device fluidly connected to the fluid aspirating cannula. The system may further include a control unit configured to receive imagery acquired using the sensor probe and analyze the imagery in real-time to determine the location.

According to another aspect, a method for performing an automated medical procedure includes positioning an effector unit over a patient, acquiring medical imagery of the patient using a sensor probe associated with the effector unit, analyzing the medical imagery using at least one processor to determine a location, and sequentially positioning a plurality of subunits of the effector unit to perform the automated medical procedure at the location, wherein each of the subunits includes a different surgical tool. The automated medical procedure may be a body fluid aspiration procedure and one of the plurality of subunits of the effector unit may be a fluid aspirating cannula subunit.

BRIEF DESCRIPTION OF THE DRAWINGS

Illustrated embodiments of the disclosure are described in detail below with reference to the attached drawing figures.

FIG. 17 illustrates one example of a screen display which may be used to monitor operation of motors and linear actuators when in a manual mode.

DETAILED DESCRIPTION

A system is provided that may be used for automated performance of a medical procedure. Although the system may be configured for different types of procedures through selection of the sensors used, the surgical tools used, and the software used, the system will be described primarily with respect to an automated body fluid aspiration system where ultrasound imaging is performed.

Figure 1:
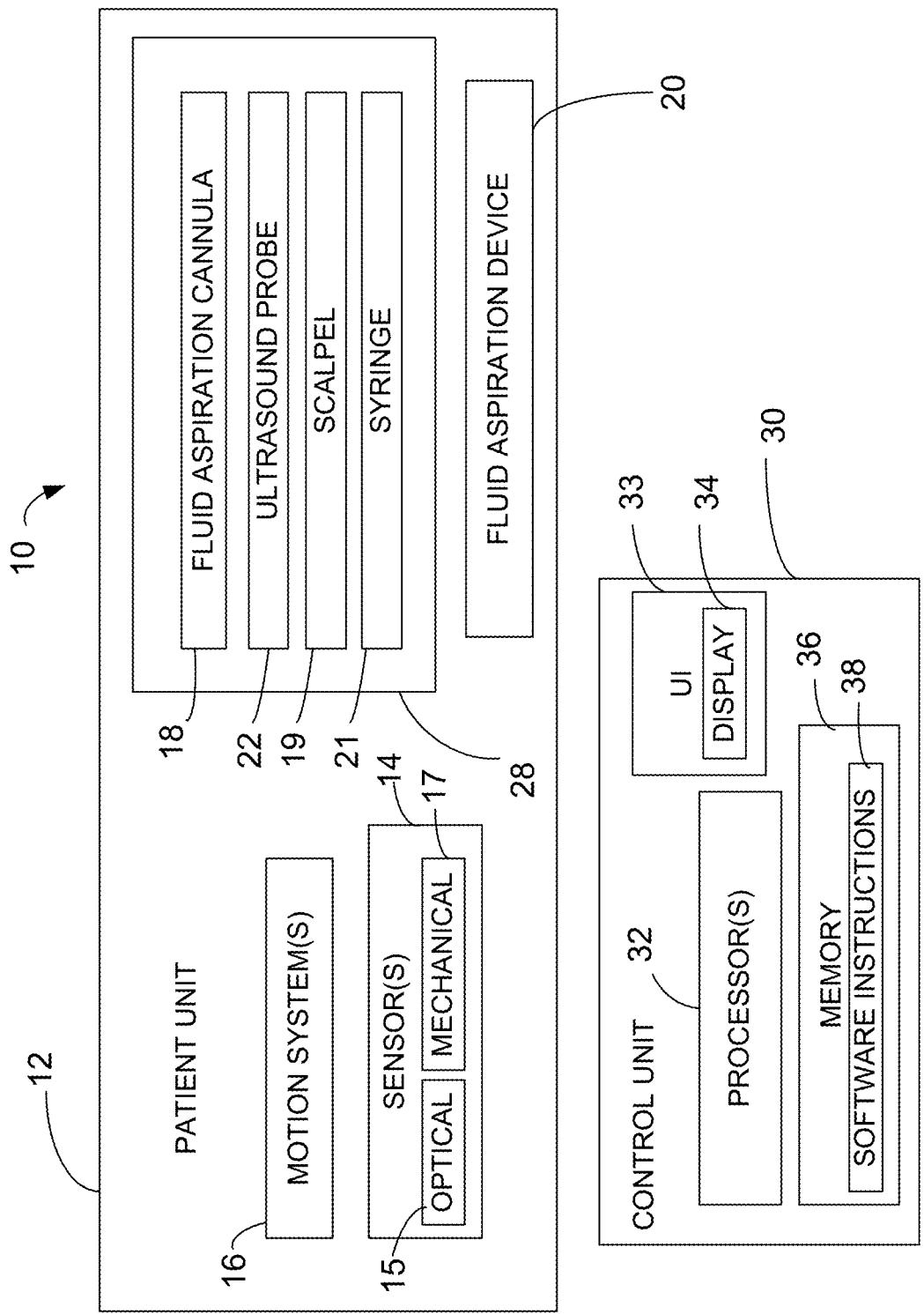
FIG. 1 is a block diagram illustrating one example of a system.

FIG. 1 is a block diagram illustrating one embodiment of a system 10. The system 10 includes a patient unit 12 and a control unit 30. The patient unit 12 may include components or tools such as a fluid aspirating cannula subunit 18, a fluid aspirating device 20, an ultrasound probe 22, a scalpel blade subunit 19, and a syringe subunit 21. Of course, other types of tools may be present.

The control unit 30 may include one or more processors 32 operatively connected to a memory 36 and operatively connected to a user interface 33 which may include a display 34. Software instructions 38 may be stored in the memory 36 and executed using the one or more processors 32. As will be explained in greater detail, the software instructions may use machine learning or other artificial intelligence (AI) based algorithms and techniques. The memory 36 may be a non-transitory machine-readable memory. The one or more processors 32 may include one or more central processing units (CPUs) and/or one or more graphics processing units (GPUs). The user interface 33 may be used to communicate status information regarding the medical procedure to a health care provider. In some embodiments, the health care provider may be located remotely. The status information may include images acquired during the procedure, sensor information, results of analysis, levels of fluid, or other information. In addition, if the health care provider is performing manual control, this may be performing the user interface 33. In some embodiments, the processor(s) 32 may include one or more processors located locally and one or more processors located remotely such as over a communications network such as the internet, another wide-area-network or over a local area network. Thus, for example, a health care provider may monitor and/or control the patient unit from a remote location. This may be advantageous where a medical procedure is to be performed by no qualified health care provider is available within the geographic area. This may also be advantageous in a situation where a patient is in isolation due to infectious disease, and thus, performing the medical procedure remotely protects against spread of the infectious disease.

One or more motion systems 16 may also be operatively connected to the control unit 30. The motion system(s) may be used for positioning one or more components of the patient unit 12. This may involve moving a gantry and/or moving a robotic head or effector unit configured to carry and deploy appropriate surgical tools. In addition one more additional sensors 14 may be operatively connected to the control unit 30 such as may be used to provide feedback regarding the motion systems 16 or additional monitoring of the orientation, position, or other state of the patient, the patient unit 12, one or more components within the patient unit 12, the environment, or any other variable which may be relevant to performance of an automated medical procedure. For example, sensors 14 may be used to measure a volume of fluid collected or drained or other parameter. Sensors 14 may also be used such as mechanical sensors 17 which may be contact sensors or touch sensors, force feedback sensors, or other types of sensors used to monitor deployment or progress of a surgical tool. The sensors 14 may also include optical sensors 15 such as cameras including time-of-flight cameras to acquire additional data. Data from the sensors 14 may be combined with data from the ultrasound probe 22 for use in control methodologies and feedback loops. For example, data from the sensors 14 and ultrasound probe 22 may be used to location a position on a patient's body for performing a procedure, to position the patient unit 12 at an appropriate location or position, to position the effector unit 28 at an appropriate position, to verify that position of the patient unit or effector unit is being maintained, to verify position of or operation of a subunit such as the fluid aspiration cannula subunit 18, the scalpel blade subunit 19, the syringe subunit 21, or other subunit, or for other purposes.

In some embodiments, the fluid aspirating cannula subunit 18 and the ultrasound probe 22 may be integrated into or otherwise associated with an effector unit 28. The one or more motion systems 16 may be used to move the effector unit to a desired location and position based on the region of interest of the patient and the function to be performed or tool to be used. It is contemplated however, that other imaging technologies may be used. It is further contemplated that other surgical tools may be used depending upon the procedure being performed.

In operation, the ultrasound probe 22 may acquire imagery of fluid within a patient by scanning the patient. Thus, for example, if the fluid is within a patient's abdomen, the ultrasound probe 22 may be used to scan the patient's abdomen. In some embodiments, one or more motion systems 16 may be used to position the ultrasound probe 22 at an appropriate location to acquire images of the fluid. This may involve moving a gantry in three dimensions so as to allow for positioning the ultrasound probe 22 and/or surgical tools.

Once acquired, the images may be analyzed by an AI driven interface in real-time. The AI driven interface may be implemented in software instructions operating on a computing device which includes one or more processors. The analysis may provide for re-positioning the ultrasound probe 22 and acquiring additional imagery. Otherwise, the AI driven interface may provide for identifying an appropriate location to aspirate fluid and guiding a needle or other tool to the location in real-time. The particular location and path taken may be selected based a variety of factors such as those which a highly skilled radiologist may apply in a manual process. For example, the location and path may be selected so as to avoid adjacent organs, maximize drainage, minimize insertion depth, or any number of other criteria as may be appropriate for a particular patient or a particular procedure. It should also be understood that when this process occurs, continuous feedback loops may be present in control methodologies to allow for monitoring of the process using available sensors whether mechanical, optical, or the imagery from the ultrasound probe 22.

Figure 2:
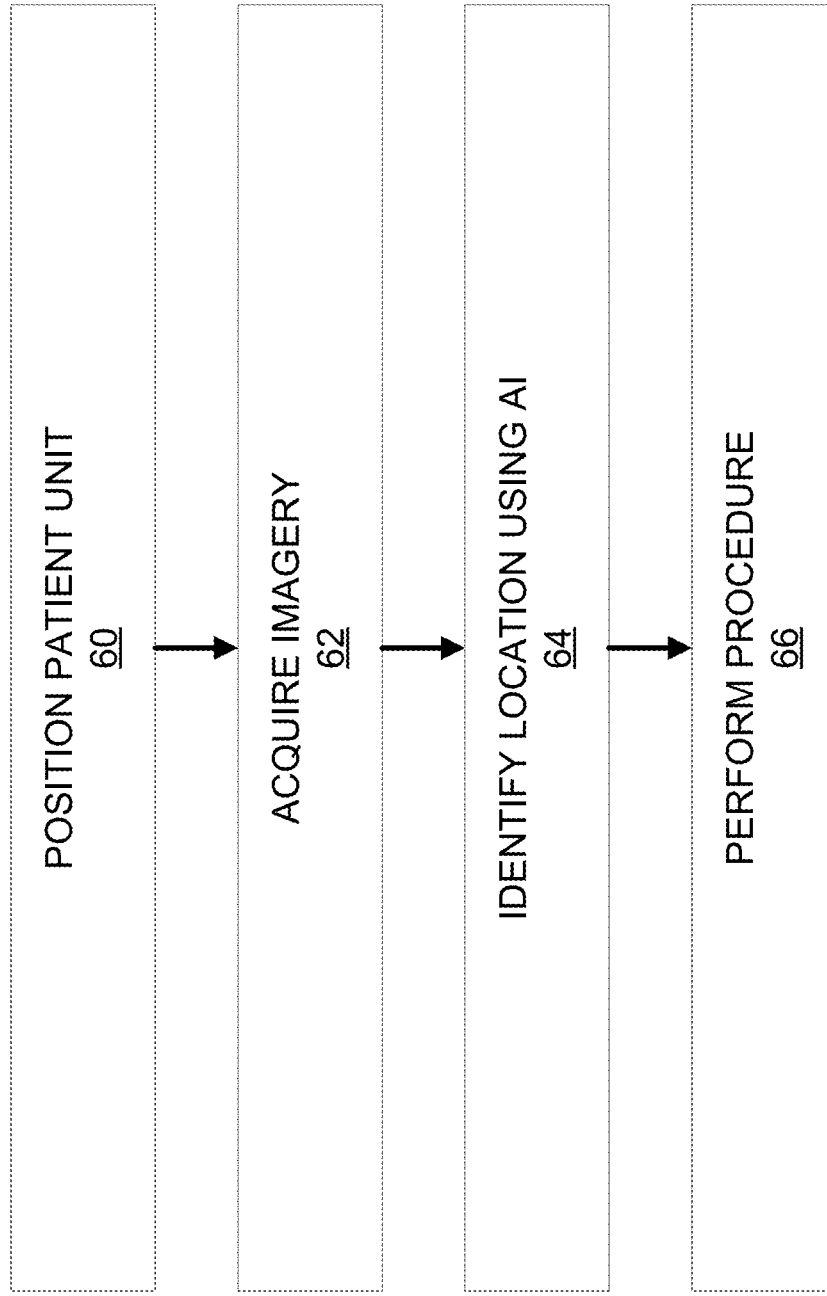
FIG. 2 is a flow diagram illustrating one example of a method.

FIG. 2 illustrates one example of a method which may be performed. In step 60, the patient unit may be positioned at an appropriate position relative to a patient. This may involve using one or more motion control systems such as to move an effector unit along a gantry or otherwise provide motion control in 3 dimensions. This may also include moving the gantry in 3 dimensions as well in order to move the patient unit. Once the patient unit is properly positioned relative to the patient, in step 62, an imagery of the patient may be acquired. For example, ultrasound imagery may be acquired using an ultrasound probe to identify abnormal body fluid in the patient. Next in step 64, a location is identified using machine learning or other AI processes which provide for image processing.

Any number of different image processing techniques may be applied to the acquired imagery. This may include techniques for image segmentation and techniques for noise removal. Image segmentation may be performed with methods such as thresholding methods, edge detection, artificial neural networks, or other methods. Noise removal may be performed with methods such as applying filters (such as but not limited to wiener filters, median filters, adaptive filters) or applying transform-based techniques (such as but not limited to using filters such as Fourier, Hilbert, and wavelet transformations).

Image processing may be performed using machine learning and/or artificial intelligence. For example, a neural network may be used such as a convolution neural network. Such networks may be trained using data acquired using the system or otherwise acquired. The image processing may be performed in real-time to identify a location from which fluid should be extracted. Software instructions may provide for the image processing or other processing needed to identify a location or spot.

In some embodiments, ultrasound imagery may be combined with data from other sensors. For example, optical sensors such as cameras or other imaging sensors may be used. Where the optical sensors provide imagery, this imagery may also be processed using any number of methods including those discussed above. In addition, machine learning and/or artificial intelligence may combine the imagery from the topical sensors with the ultrasound imagery to determine an appropriate location. In addition, in some embodiments, mechanical sensors may be used such as for contact sensing, sensing force, or other purposes. Data from mechanical sensors may be combined with data from optical sensors and/or ultrasound imagery to assist in determining location and/or to assist in monitoring location and other aspects of operation.

In step 66, the medical procedure is performed. For example, the skin may be anesthetized. The fluid aspirating cannula subunit may be driven to the location selected by the system. Once the cannula reaches the desired location the system may activate the fluid aspirating device. The system may then monitor the residual amount of fluid and may terminate the procedure accordingly to preset metrics which may be based on an amount of time, an amount of fluid left, the amount of fluid extracted, combinations thereof and other factors such as may be applied by a highly skilled radiologist.

Thus, according to one embodiment, an ultrasound probe driving subunit is used to acquire images of the fluid by scanning from the patient's abdomen. The images are analyzed by the AI driven interface in real time. After identifying an appropriate spot to aspirate fluid, the AI system may now drive the other components. For example, the effector unit may now anesthetize the skin with the syringe subunit and drive the fluid aspirating cannula subunit to the spot chosen by the system. Once the cannula reaches the desired spot, the effector unit may switch on the fluid aspirating device. The ultrasound probe subunit may continue to monitor the residual amount of fluid and terminate the procedure as per preset metrics. The effector unit may then take out the fluid aspirating cannula and the procedure is completed. The ultrasound probe, needle and cannula mechanisms may be mounted on a specialized portable gantry system which can move in three planes around the patient in a systematic fashion. The subunits used may be used in a sequential manner according to the procedure to be performed. Other subunits may be used as may be appropriate for different types of procedures.

During the procedure, the user interface of the control unit may provide a health care provider an oversight over the whole process, so it can be adequately regulated. This facility also affords to operate the system remotely. Thus, the system may be used to aspirate fluid from body cavities, e.g. ascites (fluid accumulated in the abdominal cavity) or pleural effusion (fluid accumulated in the chest cavity) or other types of body fluid aspiration.

Figure 3:
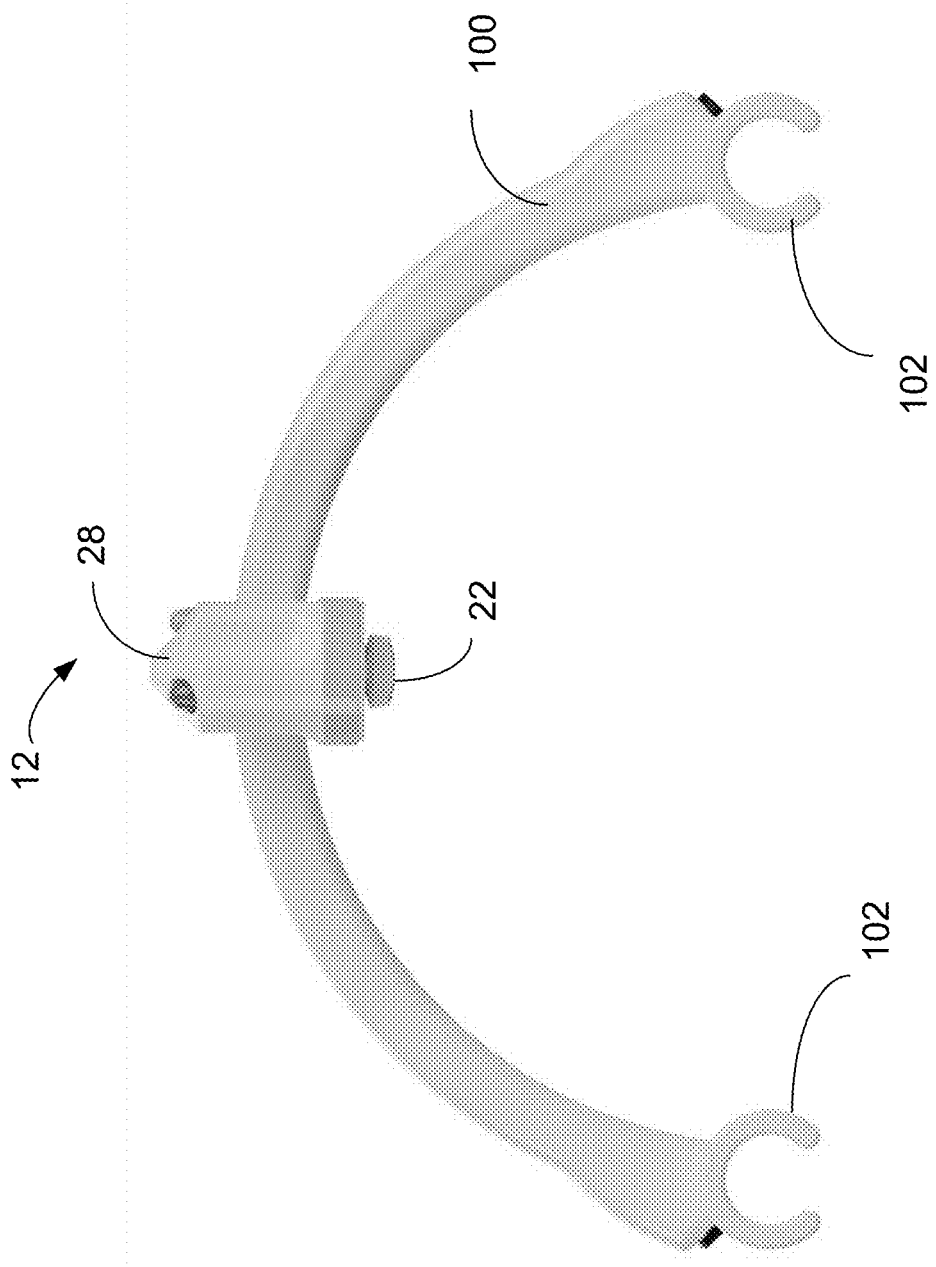
FIG. 3 illustrates one example of an arcuate or C-shaped gantry system on which the system may be mounted, with navigational capabilities in three dimensions.

FIG. 3 through FIG. 10 illustrate one embodiment of a system which may be used for performing a medical procedure. FIG. 3 illustrates one embodiment of a patient unit 12. A c-shaped gantry 100 is shown on which a functional effector unit 28 is mounted. The c-shaped gantry 100 may also be described as having an arcuate main body for arching over a patient. The effector unit 28 includes the surgical tools as well as the imaging device such as an ultrasound probe 22. The c-shaped gantry 100 may be sized and shaped so as to fit over a patient on a patient bed. First and second opposite ends 102 may fit to a railing for a patient bed. The system is light weight, easy to assemble and a patient friendly design which is compatible with existing bed systems. The c-shaped gantry 100 may move in 3 planes to allow for precise positioning within 3 dimensional space.

Figure 4:
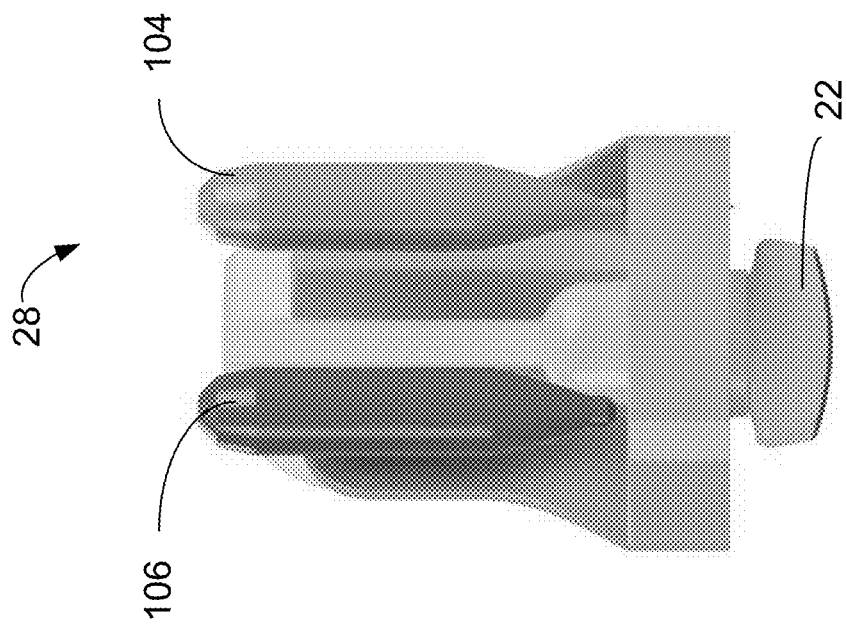
FIG. 4 illustrates a functional effector unit which may be guided by Artificial intelligence and remote navigation.

FIG. 4 is a further illustration of the effector unit 28 showing the inner portion thereof. The effector unit 28 may be guided by artificial intelligence and remote navigation. An imaging device such as an ultrasound probe 22 extends downwardly from the effector unit 28. A plurality of subunits 104, 106 are shown which provide for tools for use in performing the procedure.

Figure 5:
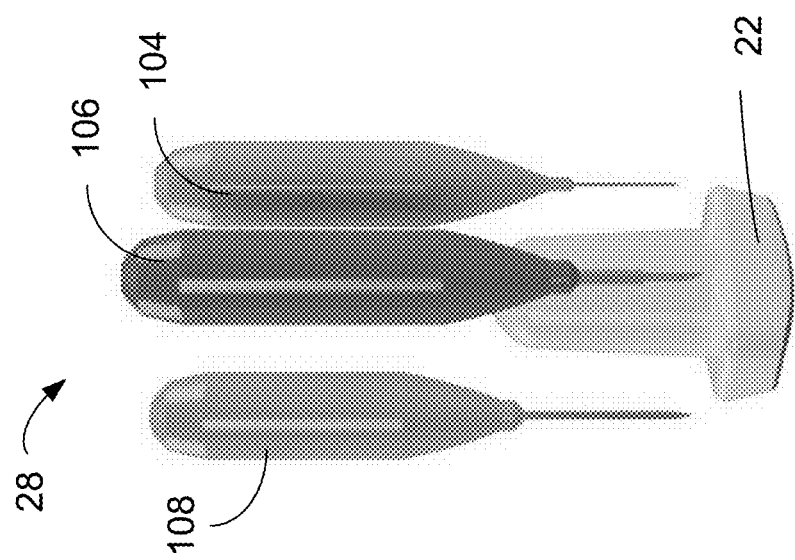
FIG. 5 is the use of ultrasound in a real time fashion but with AI driven image analysis.

FIG. 5 further illustrates the ultrasound probe 22 and a plurality of subunits 104, 106, 108 are shown. Each of the subunits may be generally tubular in design. Each of the subunits 104, 106, 108 may be arranged around the ultrasound probe 22.

Figure 6:
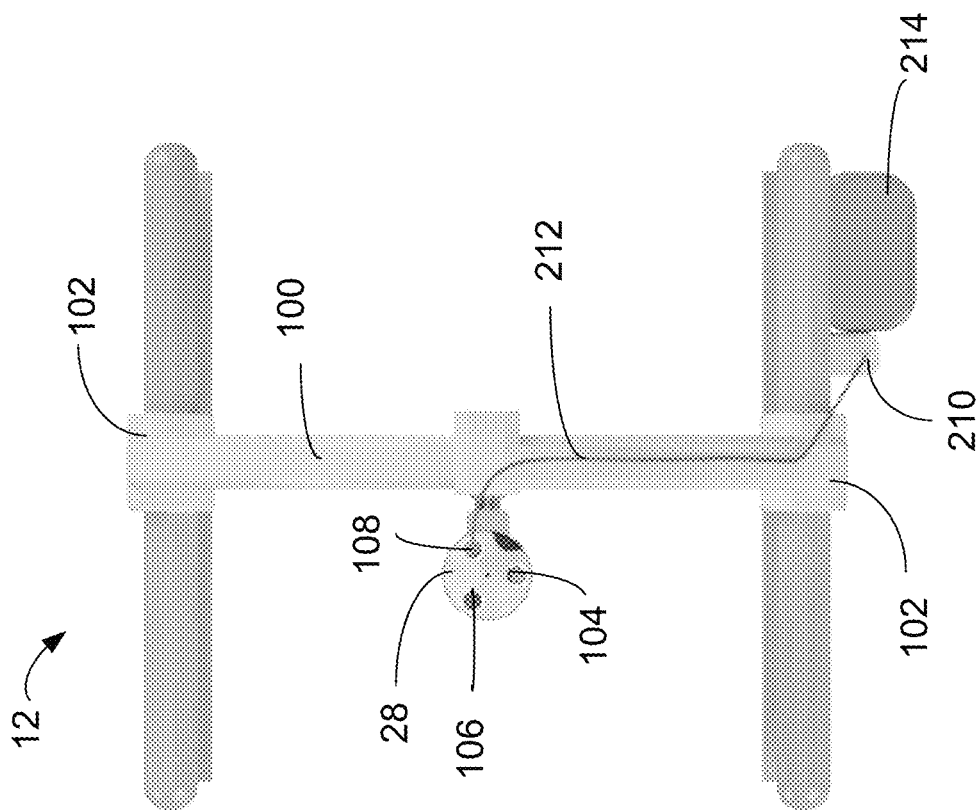
FIG. 6 illustrates subunits arranged around a sensor probe such as an ultrasound probe.

FIG. 6 further illustrates the patient unit 12. Note that the effector unit 28 is generally circular as shown and the subunits 104, 106, 108 are designed around the effector unit 28. In operation, the effector unit 28 may rotate clockwise or counterclockwise so that each of the subunits may be placed over a target spot or location merely through this rotation and without otherwise requiring re-positioning of the effector unit 28 along the gantry 100. One of the subunits such as subunit 108 may provide for a fluid aspirating cannula. The tube 212 extends to a fluid aspirating device 210 with a fluid collection container 214.

Figure 7:
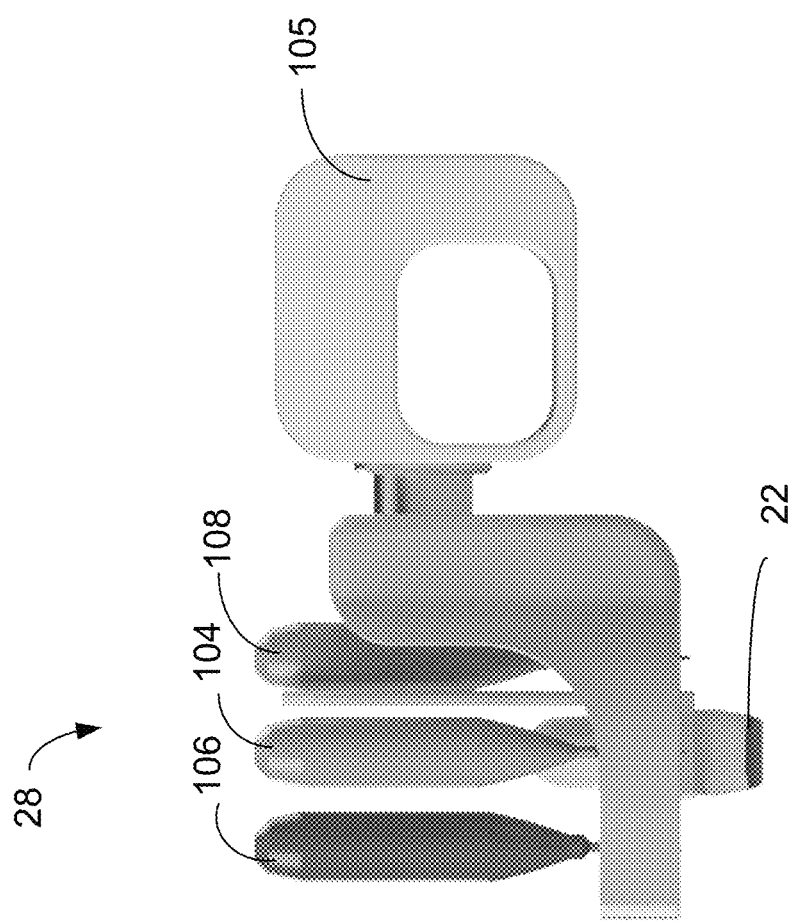
FIG. 7 is the subunit component design and their application to inject local anesthesia, scalpel blade and the aspiration cannula.

FIG. 7 further illustrates the effector unit 28. There is a gantry mount 105 for mounting to the gantry. Each of the subunits 104, 106, 108 are shown mounted around the ultrasound probe 22. The subunits may include a subunit for injection of local anesthesia, a subunit with a scalpel blade, and a subunit with an aspiration cannula. Of course, it is contemplated that other subunits may be present depending upon the specific medical procedure to be performed.

Figure 8:
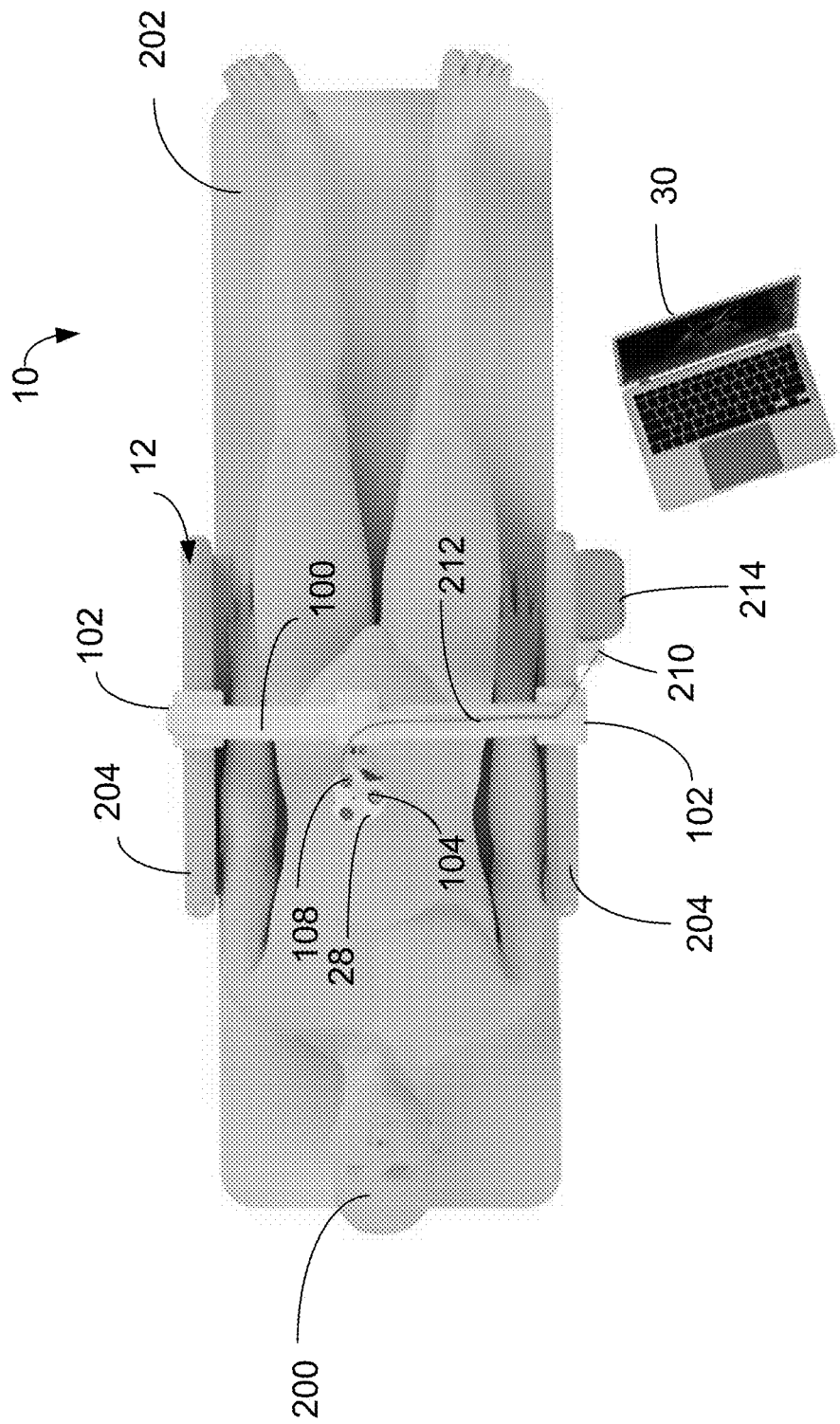
FIG. 8 is the software side, use of AI to analyze the ultrasound images in real time against preestablished ground truth.
Figure 9:
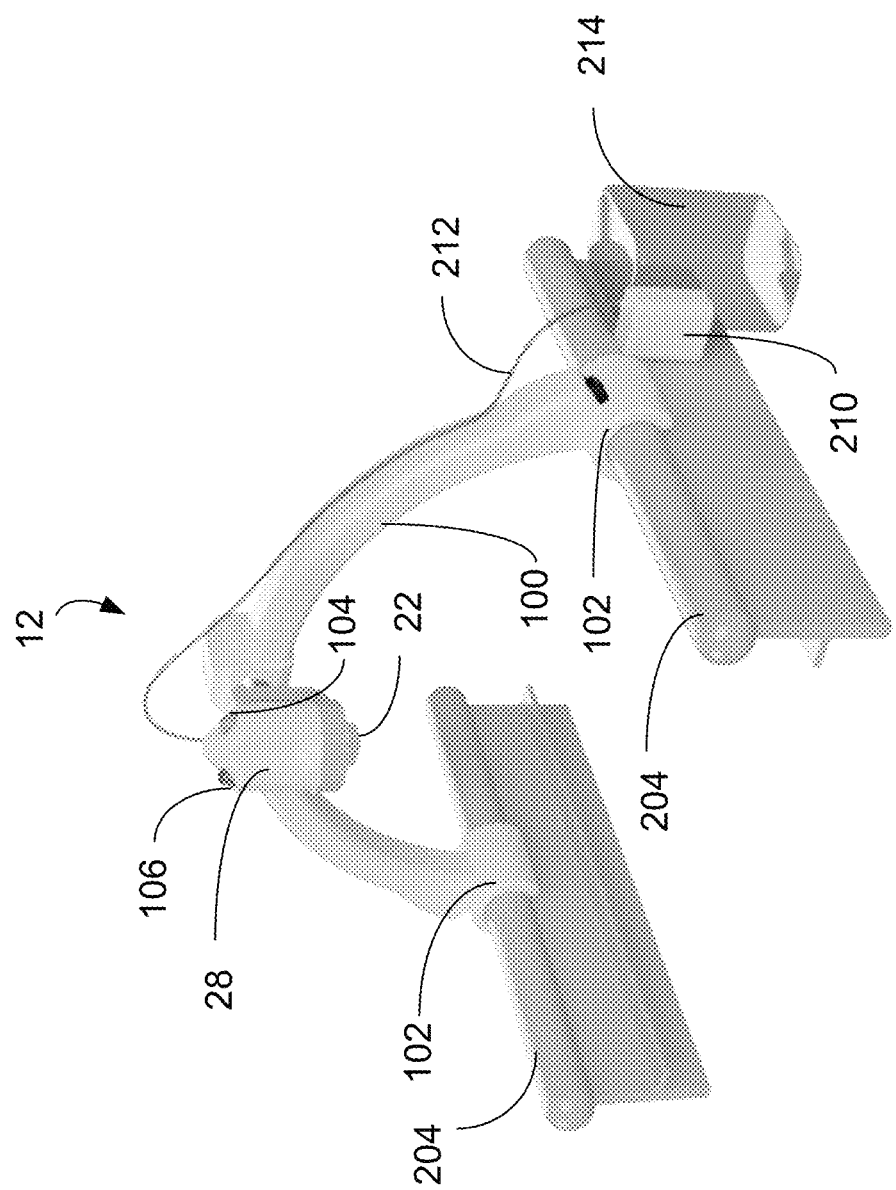
FIG. 9 further illustrates the system.
Figure 10:
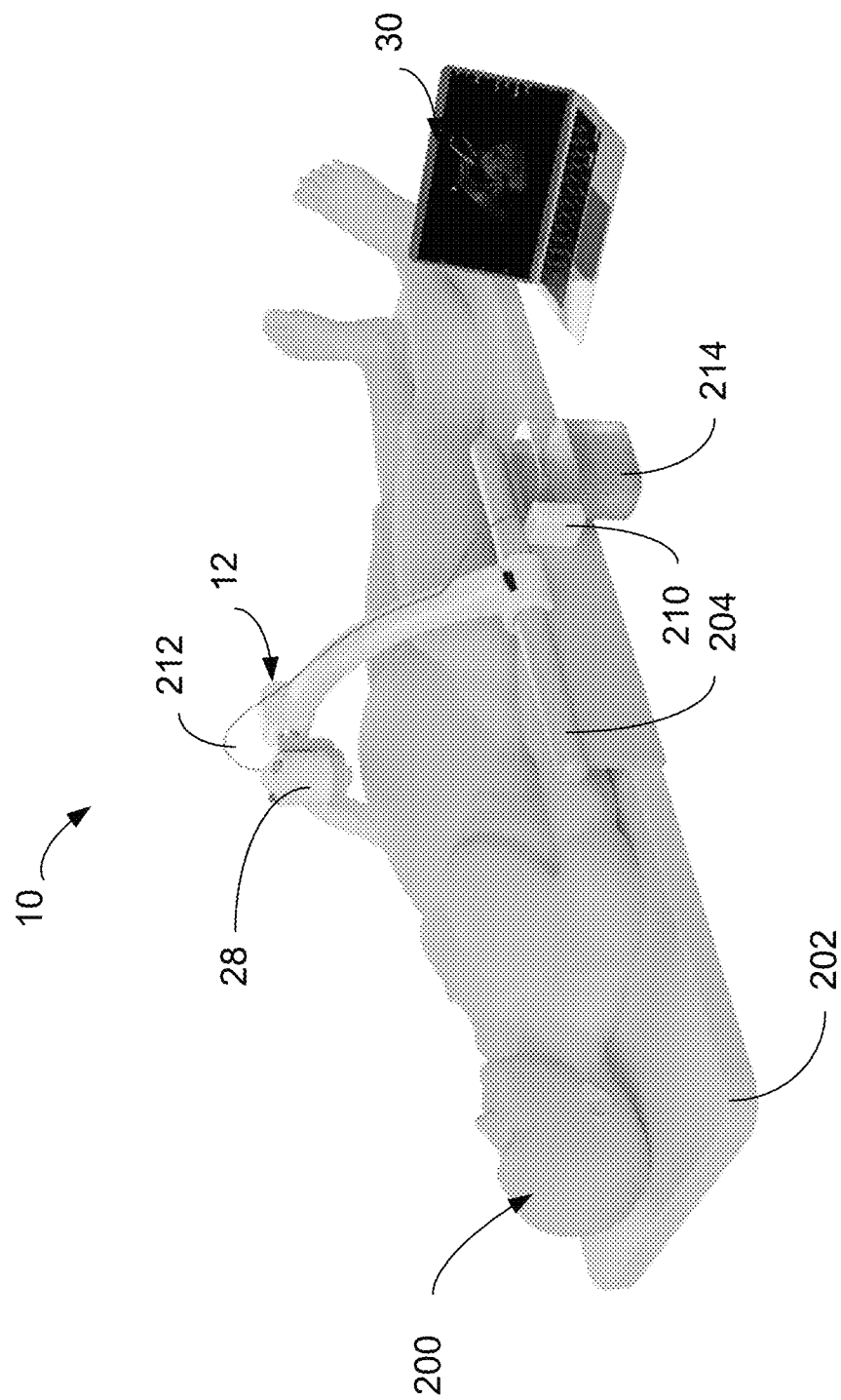
FIG. 10 further illustrates the system.

FIG. 8 further illustrates the system 10 with the gantry 100 connected to the bed rails 204 of a patient bed 202 upon which a patient 200 is placed. The system 100 includes a control unit 30 which may be in the form of a computing device is shown and may be electrically connected to the patient unit 12 or otherwise in operable communication such as through a wireless interface if used. FIG. 9 is a further view of the patient unit 12. FIG. 10 is a further view of the system 10 including a control unit 30.

FIG. 11 through FIG. 16 illustrate another example of an effector unit. The aspects of the system shown in FIG. 11 through FIG. 16 may be combined with those shown in FIG. 3 through FIG. 10. While FIG. 3 through 10 illustrate a system where the effector unit is circular and rotates to allow for selection of different subunits for different surgical tools, the example shown in FIG. 11 through FIG. 16 allows for linear movement to be used to allow for sequential selection and use of different subunits for surgical tools. It is to be understood that what is shown is merely representative and that other manners of tool selection and use may be used.

Figure 11:
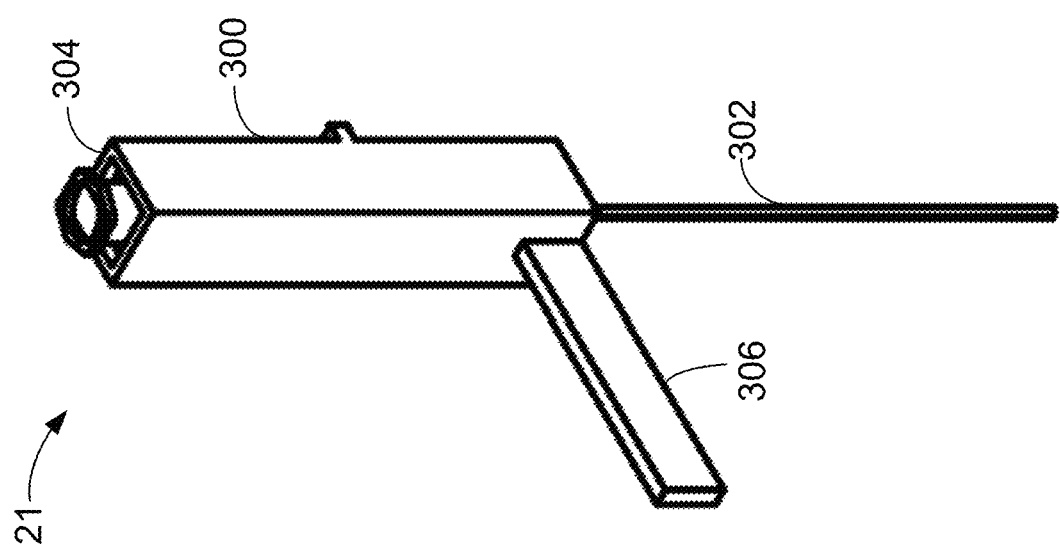
FIG. 11 illustrates one example of a syringe subunit.

FIG. 11 illustrates one example of a syringe subunit 21. The syringe subunit 21 may include a main body 300 with a syringe body 304 contained therein. A needle 302 is shown extending downwardly. A mounting member 306 is shown extending outwardly from the main body 300 for mounting the syringe subunit 21 within the effector unit.

Figure 12:
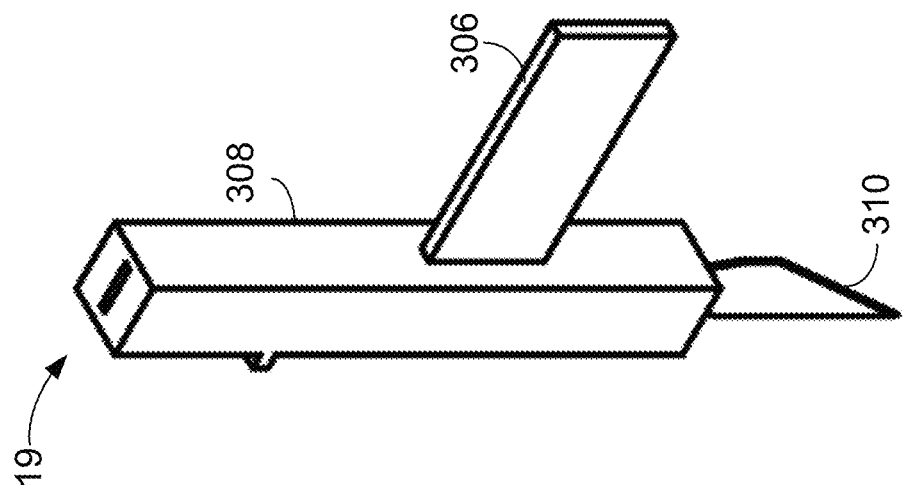
FIG. 12 illustrates one example of a scalpel subunit.

FIG. 12 illustrates one example of a scalpel subunit 19. The scalpel subunit 19 has a main body 308. A scalpel blade 310 is positioned at an end of the main body 308. A mounting member 306 is shown extending outwardly from the main body 308 for mounting the scalpel subunit 19 within the effector unit.

Figure 13:
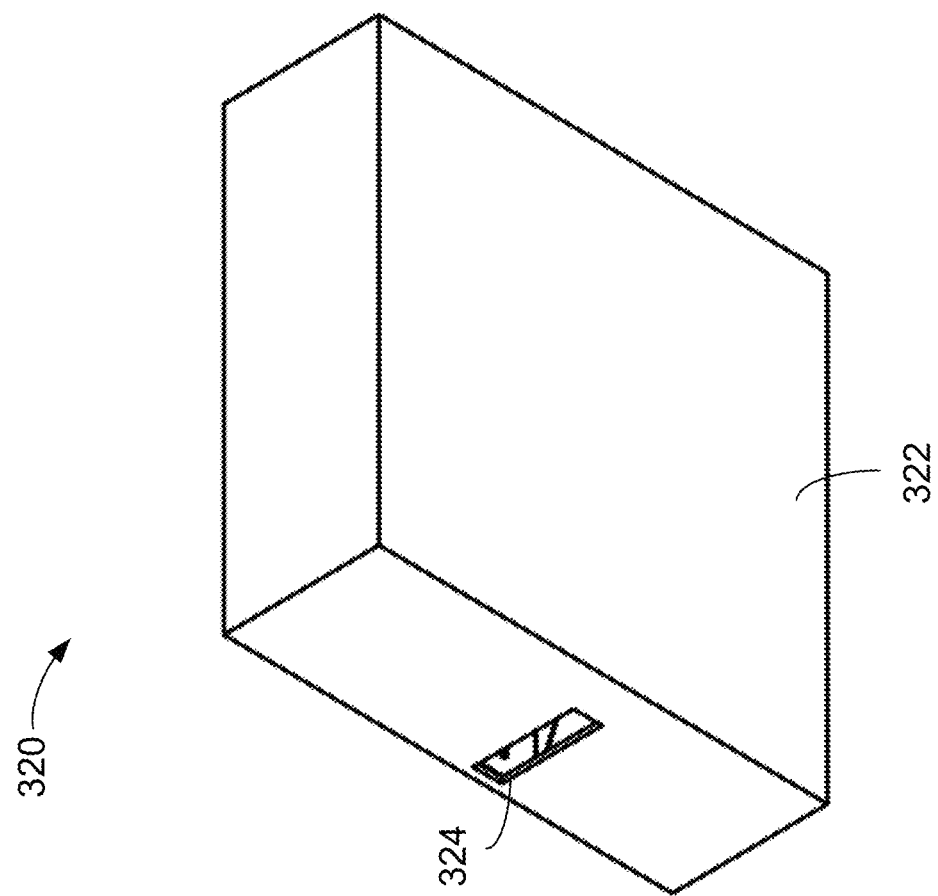
FIG. 13 illustrates another example of a subunit housing for an effector unit.

FIG. 13 illustrates another example of a subunit housing 320 for an effector unit. The subunit housing 320 has a main body 322 with an opening 324. Surgical tools may be housed within the subunit housing 320 and moved into place so that they may protrude through the opening 324.

Figure 14:
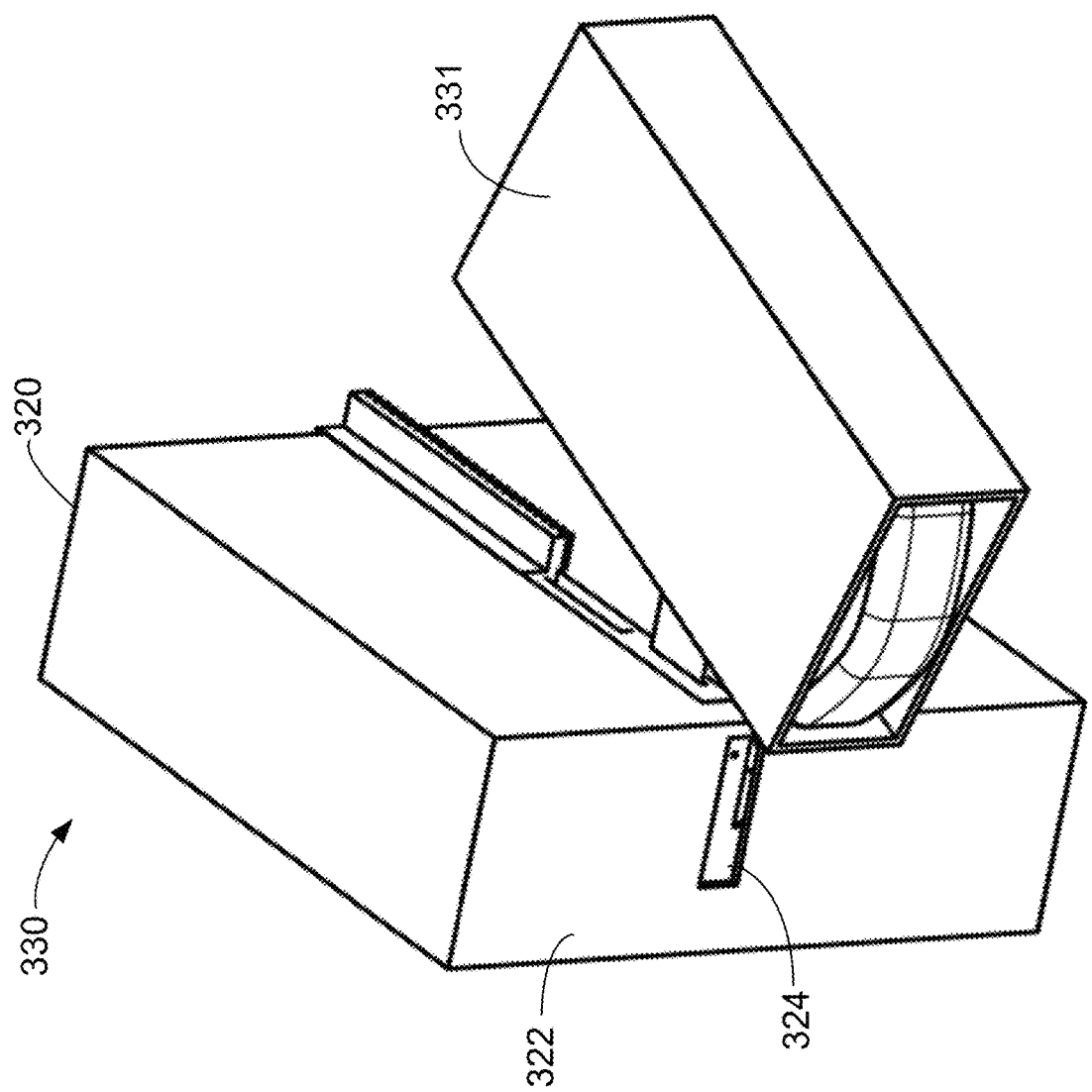
FIG. 14 illustrates an effector unit with a subunit housing.

FIG. 14 illustrates an effector unit 330 with a subunit housing 320 with an opening 324. An enclosure 331 is present such as may be used to house an ultrasound unit and the subunit housing 320 may be configured to move relative to the enclosure 331 such as rotationally and/or linearly.

Figure 15:
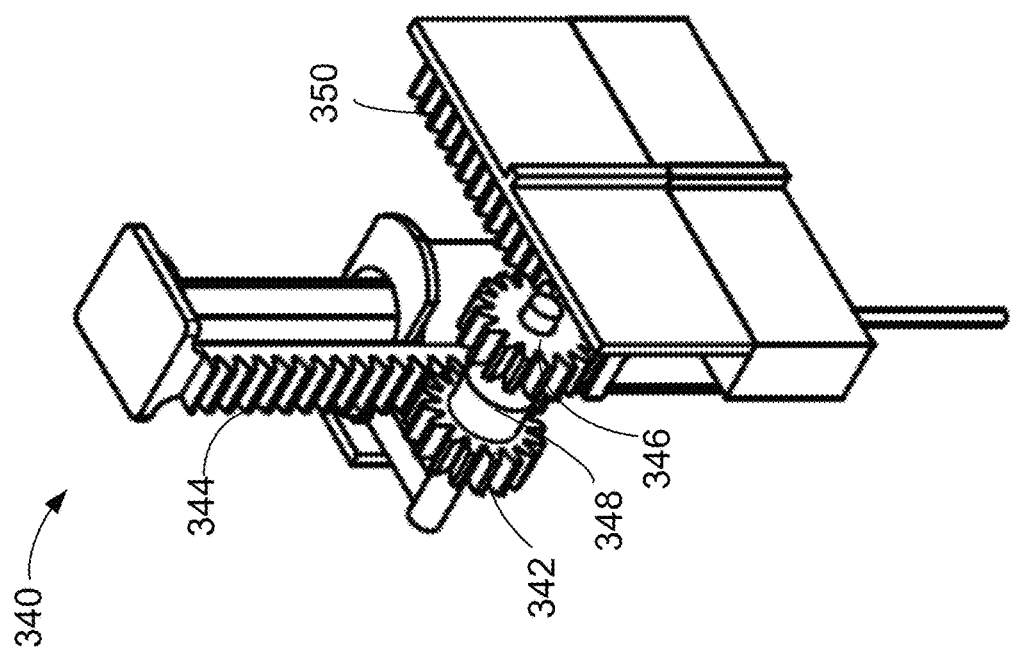
FIG. 15 illustrates an example of a syringe effector unit.

FIG. 15 illustrates on example of a syringe effector subunit 340. A linear track 350 is shown which may extend along the subunit housing. A first gear 346 is engaged in the linear track 350. A body 348 is shown with the first gear on one end and a second gear 342 at an opposite end. The second gear 342 engages a linear track 344. Note that the linear track 350 is orthogonal to the linear track 344. Thus, there is movement provided along two different axes such as in an X direction and a Y direction and a single stepper motor may be used to do so.

Figure 16:
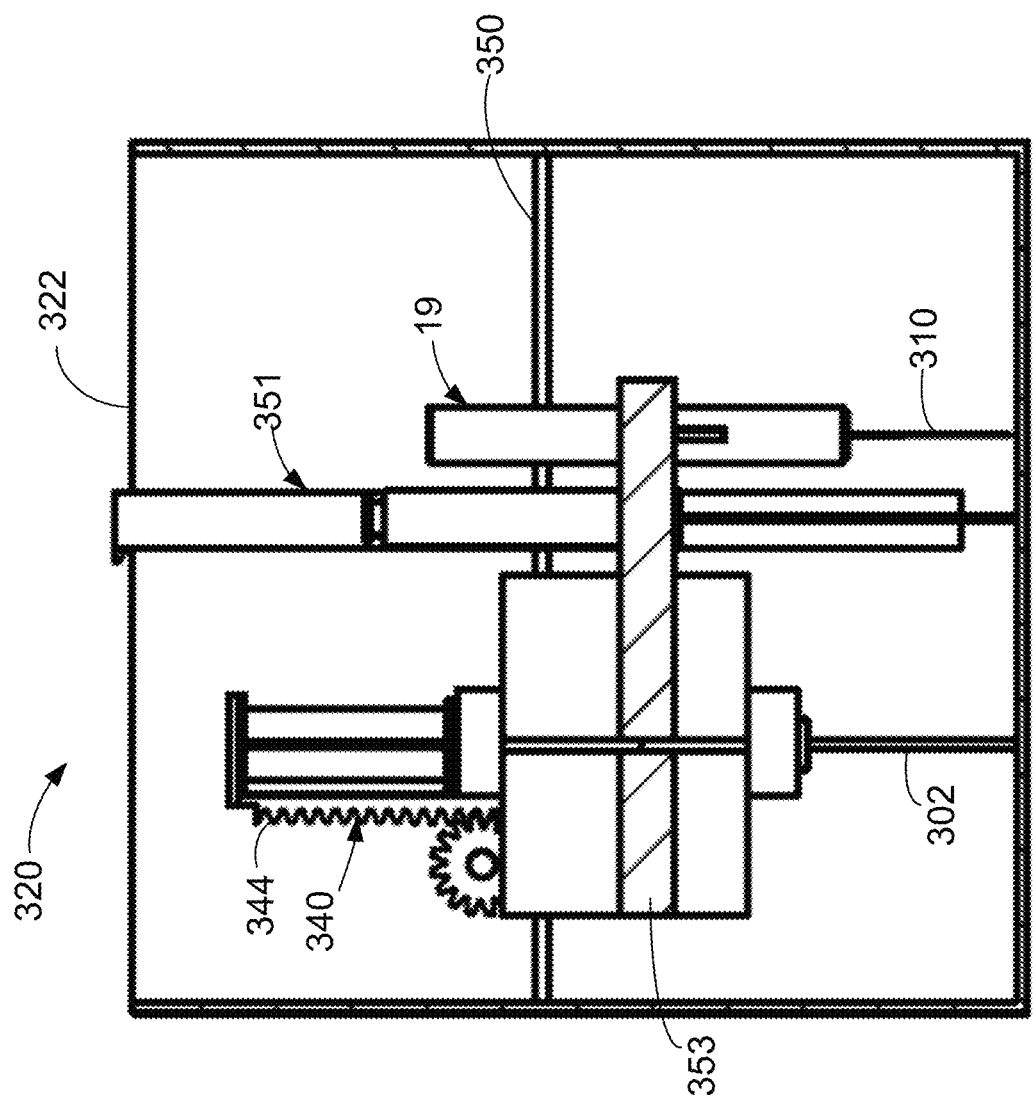
FIG. 16 illustrates the subunit housing where there are three different surgical tools mounted for sequential operation.

FIG. 16 illustrates the subunit housing 320 where there are three different surgical tools mounted for sequential operation. The syringe effector subunit 340 is shown, as well as a cannula subunit 351, and a scalpel subunit 19. The syringe effector subunit 340, the cannula subunit 351, and the scalpel subunit 19 are mounted to a mounting member 353. As shown, the cannula subunit 351 is aligned within an opening in the subunit housing 320 (not shown in this view). The various tools may be moved linearly along the track 350 in a sequential manner. One of the benefits of this particular embodiment is that fewer actuators are used and less space is needed than if all of the various surgical tools are separately housed and independently moved independently.

Thus, as shown, horizontal movement may be used to select the appropriate tool, for example the syringe effector unit 340 for needle insertion for local anesthetic, the scalpel unit 19 for skin incision, and the cannula unit 351 for fluid aspiration. In other words, the linear track 350 allows for sequential activation of different tools. In addition, vertical movement may be imparted once the proper tool is aligned with the opening. Any number of sensors may also be present including contact sensors to assist in monitoring the procedure as previously explained. In addition, each of the subunits may have a linear actuator (not shown) for further positioning the subunit.

Figure 17:
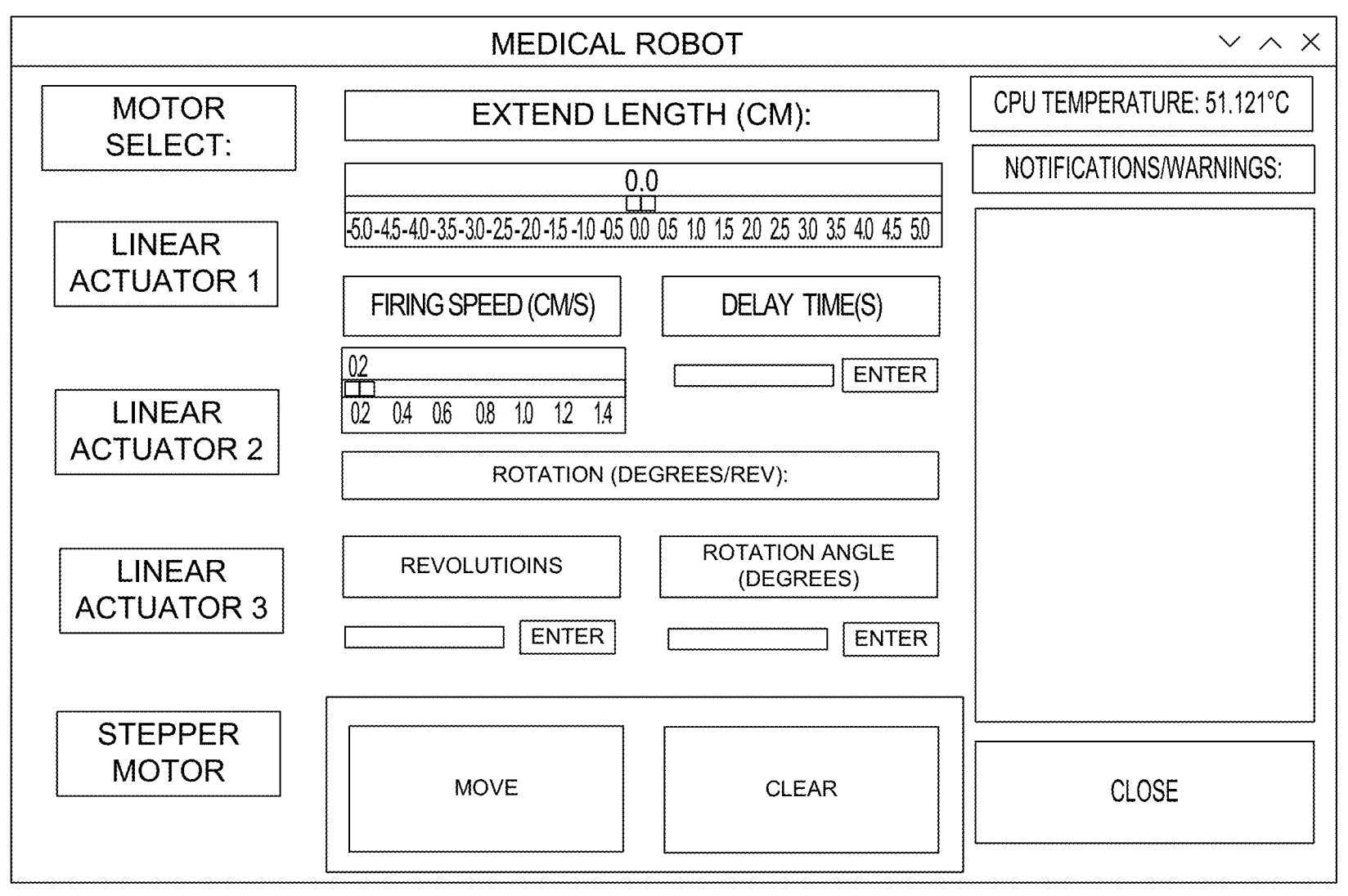
Figure 18:
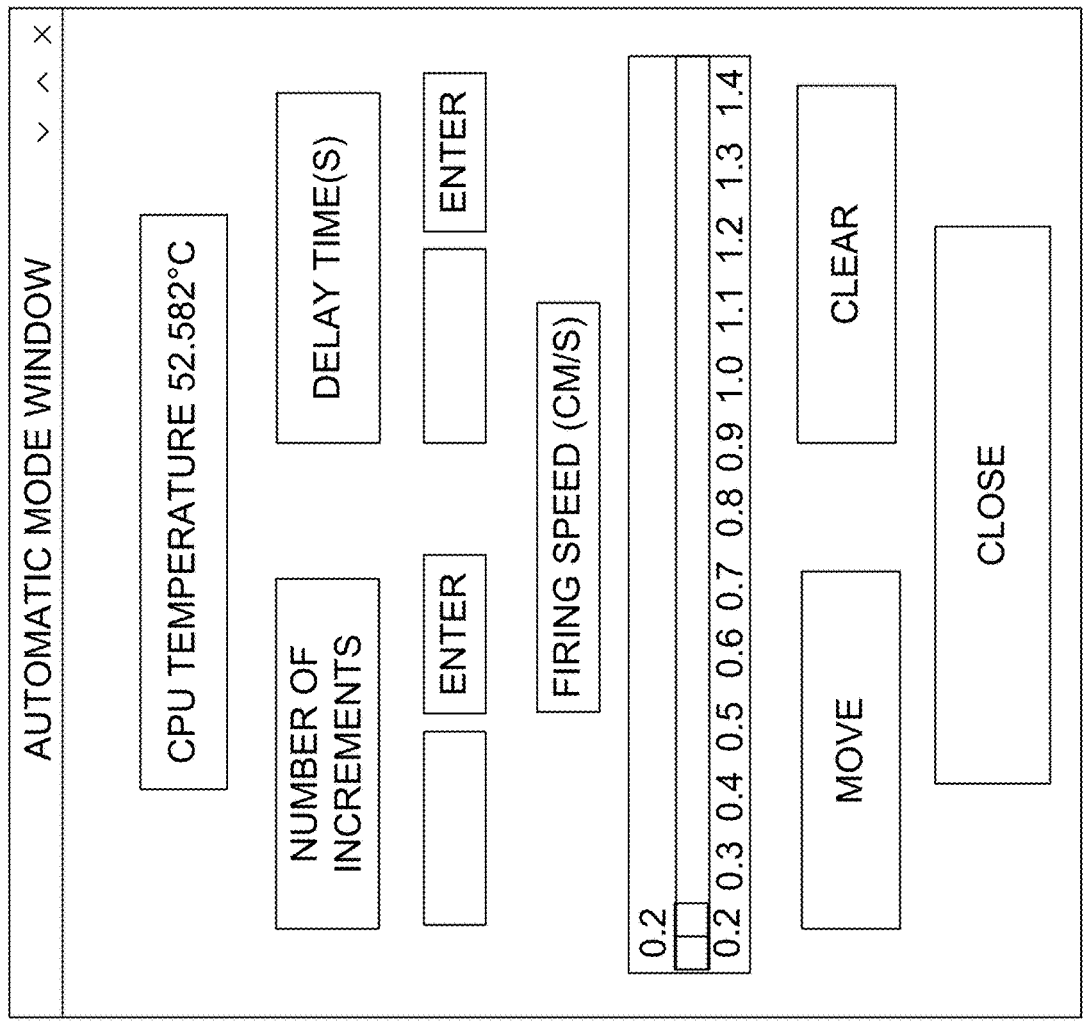
FIG. 18 illustrates one example of a screen display which may be used to monitor operation of motors and linear actuators when in an automatic mode.

FIG. 17 illustrates one example of a screen display which may be used to monitor operation of motors and linear actuators. In the embodiment shown in FIGS. 11 through 16, a single stepper motor may be used along with linear actuators to position the subunits within the effector unit. It should be understood, that although the process is performed automatically in an automatic mode, a manual mode such as shown in in FIG. 17 may also be used in which a user can select the stepper motor or one of the linear actuators and impart movement thereto. FIG. 18 illustrates a screen display associated with an automatic mode. It should be understood that the user interface may be remote from the patient unit, such as in a different room, a different facility, across the country, or further. Thus, a medical procedure may be observed by a surgeon or other health care provider not physically present with a patient.

Figure 19:
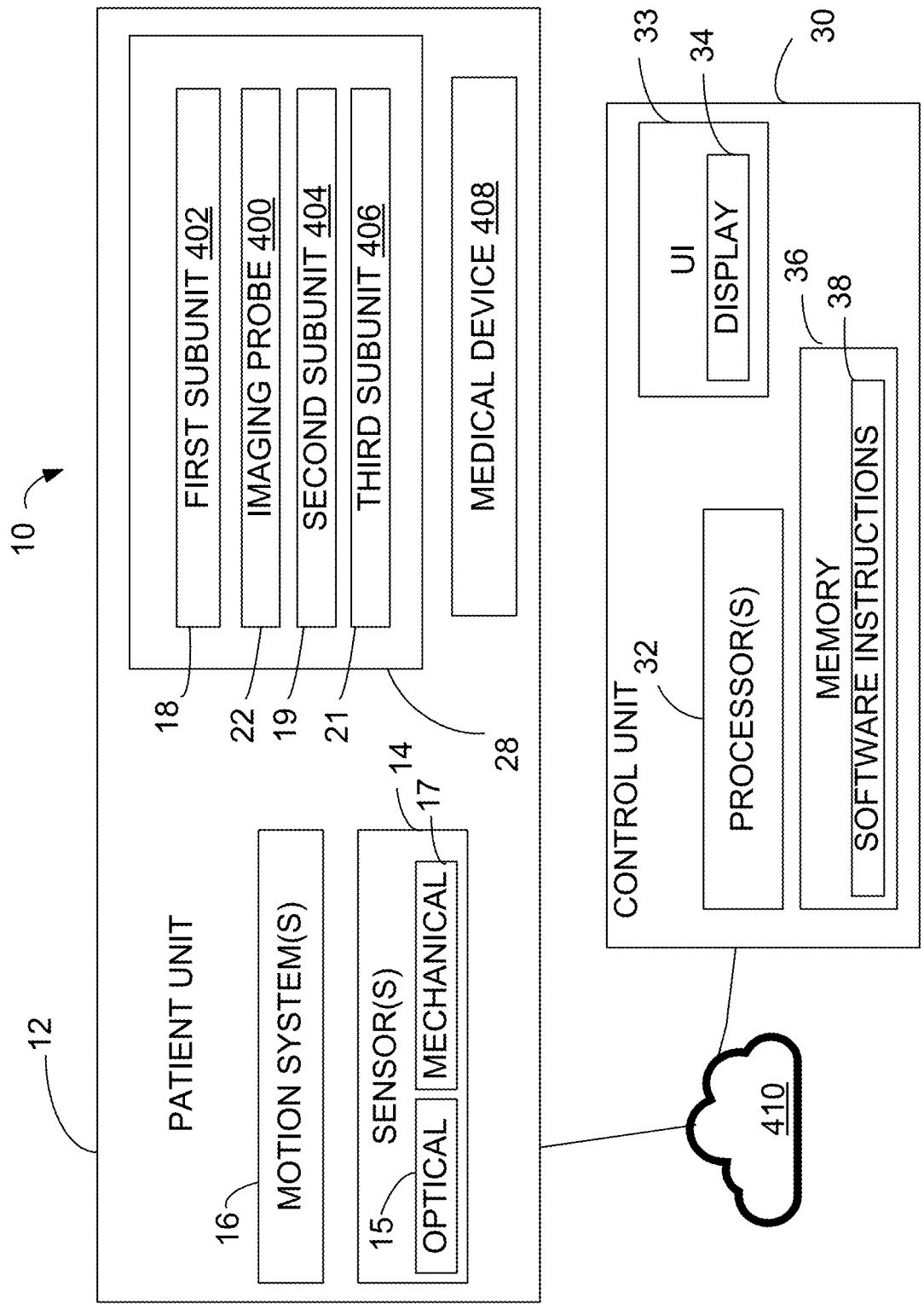
FIG. 19 illustrates another example of the system.

FIG. 19 illustrates another view of the system 10. In FIG. 19, there is an imaging probe 400, and multiple subunits 402, 404, 406 present in the effector unit 28. It should be understood, that the subunits 402, 404, 406 may provide for any number of different types tools used in performing a medical procedure. In addition, a medical device 408 is shown which may also be used in the medical procedure. The patient unit 12 may be operatively connected to the control unit 30 over a network 410 to allow for medical procedures to be performed remotely.

Although various embodiments have been shown and described the present invention contemplates numerous options, variations, and alternatives. For example, although emphasis has been on body fluid aspiration, other types of medical procedures may be performed. In addition, any number of different subunits may be used which provide different surgical tools or functions depending upon the medical procedure(s) to be performed. Although a gantry and effector unit are shown and described, it is contemplated that three-dimensional placement of the sensor probe and of the subunits may be otherwise controlled. For example, a KUKA robot or another off-the shelf robot may be used to maneuver around a patient. It is to be understood that any number of analysis may be performed for determining where to position the sensor probe or other components of the system, to evaluate acquired images, and to monitor performance of the medical procedure. It is further contemplated that the control unit may be in the form of a computer which includes one or more processors to perform real-time analysis and any number of feedback loops may be used to control the process. Although an ultrasound probe may be used, it is contemplated that other types of imaging systems may be used instead of or in addition to the ultrasound probe.

Thus, dedicated sequential automatized execution of multiple surgical steps is provided. According to one example of a series of surgical steps. This may involve first anesthetizing the skin with a first subunit, making a skin incision using a second subunit, then inserting a surgical tool such as a surgical cannula or needle into the body using a third subunit. Of course, the device may be adapted to any number of different surgical processes or procedures as these are basic fundamental steps in any surgical procedure.

For example a first subunit may be used for automatized injection involving a syringe and needle such as to inject toxic radioactive substances or Chemotherapy drugs into a patient. This may be done in a remote fashion without exposing the health care personnel. Where a scalpel subunit is used, it may be modified to do other types of surgical procedures, thereby reducing the work of surgeons. Where a surgical cannula or needle is used as a subunit, it may be modified to inject treatments in the body. Such subunits may also be adapted to do biopsies on tissues. Similarly, this functionality can be used to introduce energy emitting devices like microwave probes, radiofrequency probes, laser probes etc. in the body for treatment purposes. Similarly, a surgical cannula may be used to drain abscesses and other body organs, e.g. urinary bladder, obstructed kidneys etc. In addition, to these types of procedures, sequential actions may also be used to do other types of diagnostic and therapeutic procedures remotely, e.g. accessing blood vessels to do angiograms, venograms etc. In short by changing the tools on this device/robot, multiple diagnostic and therapeutic procedures can be performed in an automatized fashion and these procedures can be controlled locally as well as in a remote fashion. The remote functionality of the device has applications where safety of the health care professional is needed. For example in infective pandemic situations like Covid the health care personnel does not get exposed to the infected patient directly. Thus, the present invention contemplates numerous options, variations, and alternatives.

What is claimed is:

1. A system for automated body fluid aspiration, the system comprising:
   an effector unit having a housing;
   a plurality of subunits integrated into the effector unit wherein each of the subunits comprises a surgical tool and where each of the plurality of subunits is configured for independent movement relative to other subunits within the plurality of subunits;
   an ultrasound probe operatively connected to the effector unit;
   wherein one of the plurality of subunits is a fluid aspirating cannula subunit disposed within the housing of the effector unit;
   a control unit operatively connected to the effector unit;
   wherein the control unit is configured for positioning the effector unit and the plurality of subunits to sequentially target a location for performance of the automated body fluid aspiration;
   wherein the control unit is configured for acquiring imagery from the ultrasound probe and analyzing the imagery in determining the target location on a patient to aspirate body fluid and in monitoring performance of the automated body fluid aspiration during the automated body fluid aspiration;
   wherein the control unit is configured for performing automated body fluid aspiration at the location using the fluid aspirating cannula subunit.

2. The system of claim 1 further comprising a plurality of sensors operatively connected to the control unit and wherein the control unit is further configured for using data from the plurality of sensors with the imagery in determining the target location on the patient to aspirate the body fluid.

3. The system of claim 2 wherein the plurality of sensors include at least one touch sensor and at least one optical sensor.

4. The system of claim 1 further comprising a gantry and wherein the effector unit is operatively connected to the gantry.

5. The system of claim 4 wherein the gantry comprises an arcuate body for arching over the patient.

6. The system of claim 1 further comprising a fluid aspiration device fluidly connected to the fluid aspirating cannula subunit and wherein the control unit is operatively connected to the fluid aspiration device.

7. The system of claim 1 wherein the performing the automated body fluid aspiration includes inserting a needle into the patient using a syringe subunit of the effector unit, inserting a cannula using the fluid aspirating cannula subunit of the effector unit, and monitoring the imagery during aspiration of the body fluid.

8. The system of claim 7 wherein the fluid aspiration cannula subunit and the syringe subunit are linearly arranged in the effector unit for sequential operation.

9. The system of claim 1 wherein the control unit includes a display and wherein status of the automated body fluid aspiration is provided on the display.

10. The system of claim 1 wherein the control unit is configured for analyzing the imagery using a machine learning algorithm.

11. The system of claim 1 wherein the effector unit is configured to rotate.

12. The system of claim 1 wherein the plurality of subunits further comprises a syringe subunit and a scalpel blade subunit.

13. A system for automated performance of medical procedures on a patient, the system comprising:
    a gantry;
    an effector unit movably mounted to the gantry such that the effector unit is configured to move along the gantry;
    a sensor probe operatively connected to the effector unit;
    a plurality of subunits integrated into the effector unit wherein each of the subunits comprises a surgical tool, wherein each of the plurality of subunits is configured for independent movement relative to other ones of the plurality of subunits;
    wherein the effector unit is configured to re-position the plurality of subunits to sequentially target a location for the performance of the medical procedure.

14. The system of claim 13 wherein the gantry comprises an arcuate body for extending over and across a bed.

15. The system of claim 13 wherein the plurality of subunits includes at least one of an aspiration cannula subunit, a syringe subunit, and a scalpel blade subunit.

16. The system of claim 13 wherein the plurality of surgical tools includes an aspiration cannula and wherein the system further includes a fluid aspiration device fluidly connected to the fluid aspirating cannula.

17. The system of claim 13 further comprising a control unit configured to receive imagery acquired using the sensor probe and analyze the imagery in real-time to determine the location.

18. A method for performing an automated medical procedure, the method comprising:
    positioning an effector unit over a patient;
    acquiring medical imagery of the patient using a sensor probe associated with the effector unit during the automated medical procedure;
    analyzing the medical imagery using at least one processor to determine a location and monitor performance of the automated medical procedure during the automated medical procedure;
    independently and sequentially positioning a plurality of subunits integrated into the effector unit to perform the automated medical procedure at the location, wherein each of the subunits includes a different surgical tool and wherein the positioning is based on the medical imagery.

19. The method of claim 18 wherein the automated medical procedure is a body fluid aspiration and wherein one of the plurality of subunits of the effector unit is a fluid aspirating cannula subunit.

* * * * *